United States Patent
Schmidt et al.

(10) Patent No.: US 10,981,008 B2
(45) Date of Patent: *Apr. 20, 2021

(54) DELIVERY DEVICES AND METHODS FOR LEADLESS CARDIAC DEVICES

(71) Applicant: Cardiac Pacemakers, Inc., St. Paul, MN (US)

(72) Inventors: Brian L. Schmidt, White Bear Lake, MN (US); Benjamin J. Haasl, Forest Lake, MN (US); Keith R. Maile, New Brighton, MN (US); Eric Bielefeld, Floyds Knobs, IN (US); Dana Sachs, Pine City, MN (US); Adwait Kumar, Prospect, KY (US); Indaka Gunasekara, Louisville, KY (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 155 days.

This patent is subject to a terminal disclaimer.

(21) Appl. No.: 16/291,529

(22) Filed: Mar. 4, 2019

(65) Prior Publication Data
US 2019/0192816 A1    Jun. 27, 2019

Related U.S. Application Data

(63) Continuation of application No. 14/452,654, filed on Aug. 6, 2014, now Pat. No. 10,265,503.
(Continued)

(51) Int. Cl.
*A61N 1/362* (2006.01)
*A61M 25/00* (2006.01)
(Continued)

(52) U.S. Cl.
CPC ......... *A61N 1/362* (2013.01); *A61M 25/0082* (2013.01); *A61M 25/0147* (2013.01); *A61N 1/056* (2013.01); *A61N 1/3756* (2013.01)

(58) Field of Classification Search
CPC .............. A61N 1/3756; A61N 1/37205; A61N 1/0573; A61N 1/05; A61N 1/0587;
(Continued)

(56) References Cited

U.S. PATENT DOCUMENTS

| 721,869 A | 3/1903 | Dunning |
| 3,717,151 A | 2/1973 | Collett |

(Continued)

FOREIGN PATENT DOCUMENTS

| CA | 1003904 A1 | 1/1977 |
| DE | 2053919 A1 | 5/1972 |

(Continued)

OTHER PUBLICATIONS

Spickler, et al. "Totally Self-Contained Intracardiac Pacemaker" J. Electrocardiology, vol. 3, Nos. 3 & 4, pp. 325-331 (1970).

*Primary Examiner* — Mohamed G Gabr
(74) *Attorney, Agent, or Firm* — Seager, Tutte & Wickhem LLP

(57) ABSTRACT

Delivery devices, systems, and methods for delivering implantable leadless pacing devices are disclosed. An example delivery device may include a proximal section including a deflection mechanism for deflecting the proximal section, and a distal holding section extending distally of a distal end of the proximal section and defining a cavity therein for receiving an implantable leadless pacing device. The delivery device may include more than one deflection mechanism for deflecting the proximal section at multiple deflection regions. The delivery device may include more than one tubular member that are translatable relative to one another, and the one or more tubular members may include fixed curve portions. The delivery device may include an atraumatic or bumper tip at the distal end of the holding section.

20 Claims, 9 Drawing Sheets

Related U.S. Application Data

(60) Provisional application No. 61/866,715, filed on Aug. 16, 2013.

(51) Int. Cl.
*A61M 25/01* (2006.01)
*A61N 1/05* (2006.01)
*A61N 1/375* (2006.01)

(58) Field of Classification Search
CPC ........ A61N 1/059; A61N 1/372; A61N 1/056; A61N 1/057; A61N 1/375; A61N 2001/058; A61N 2001/0578; A61B 17/3468; A61B 5/0215; A61B 5/076; A61B 5/6882; A61B 5/0031; A61B 5/042; A61B 2017/22035; A61M 25/0082; A61M 25/0147; A61M 25/00; A61M 25/0068; A61M 25/0069; A61M 25/0074; A61M 25/0141; A61M 2025/0081; A61M 2025/0161; A61M 39/0208
USPC ................................. 606/129; 604/528, 529
See application file for complete search history.

(56) References Cited

U.S. PATENT DOCUMENTS

| | | |
|---|---|---|
| 3,754,555 A | 8/1973 | Schmitt |
| 3,814,104 A | 6/1974 | Irnich et al. |
| 3,835,864 A | 9/1974 | Rasor et al. |
| 3,902,501 A | 9/1975 | Citron et al. |
| 3,943,936 A | 3/1976 | Rasor |
| 3,971,364 A | 7/1976 | Fletcher et al. |
| 3,976,082 A | 8/1976 | Schmitt |
| 4,103,690 A | 8/1978 | Harris |
| 4,112,952 A | 9/1978 | Thomas et al. |
| 4,269,198 A | 5/1981 | Stokes |
| 4,280,512 A | 7/1981 | Karr |
| 4,301,815 A | 11/1981 | Doring |
| 4,402,328 A | 9/1983 | Doring |
| 4,409,994 A | 10/1983 | Doring |
| 4,502,492 A | 3/1985 | Bornzin |
| 4,531,943 A | 7/1985 | Van Tassel et al. |
| 4,662,382 A | 5/1987 | Sluetz et al. |
| 4,886,065 A | 12/1989 | Collins, Jr. |
| 4,898,577 A | 2/1990 | Badger et al. |
| 4,913,164 A | 4/1990 | Greene et al. |
| 4,989,577 A | 2/1991 | Bixby |
| 5,003,990 A | 4/1991 | Osypka |
| 5,057,114 A | 10/1991 | Wittich et al. |
| 5,129,749 A | 7/1992 | Sato |
| 5,171,233 A | 12/1992 | Amplatz et al. |
| 5,193,540 A | 3/1993 | Schulman et al. |
| 5,238,004 A | 8/1993 | Sahatjian et al. |
| 5,257,634 A | 11/1993 | Kroll |
| 5,282,845 A | 2/1994 | Bush et al. |
| 5,300,107 A | 4/1994 | Stokes et al. |
| 5,318,528 A | 6/1994 | Heaven et al. |
| 5,336,253 A | 8/1994 | Gordon et al. |
| 5,405,367 A | 4/1995 | Schulman et al. |
| 5,405,374 A | 4/1995 | Stein |
| 5,411,535 A | 5/1995 | Fujii et al. |
| 5,425,756 A | 6/1995 | Heil et al. |
| 5,443,492 A | 8/1995 | Stokes et al. |
| 5,492,119 A | 2/1996 | Abrams |
| 5,522,875 A | 6/1996 | Gates et al. |
| 5,522,876 A | 6/1996 | Rusink |
| 5,545,201 A | 8/1996 | Helland et al. |
| 5,545,206 A | 8/1996 | Carson |
| 5,557,210 A | 9/1996 | Cappa et al. |
| 5,562,723 A | 10/1996 | Rugland et al. |
| 5,575,814 A | 11/1996 | Giele et al. |
| 5,578,068 A | 11/1996 | Laske et al. |
| 5,697,936 A | 12/1997 | Shipko et al. |
| 5,716,390 A | 2/1998 | Li |
| 5,716,391 A | 2/1998 | Grandjean |
| 5,755,764 A | 5/1998 | Schroeppel |
| 5,762,637 A | 6/1998 | Berg et al. |
| 5,776,178 A | 7/1998 | Pohndorf et al. |
| 5,807,399 A | 9/1998 | Laske et al. |
| 5,837,006 A | 11/1998 | Ocel et al. |
| 5,837,007 A | 11/1998 | Altman et al. |
| 5,851,226 A | 12/1998 | Skubitz et al. |
| 5,871,531 A | 2/1999 | Struble |
| 5,908,381 A | 6/1999 | Aznoian et al. |
| 5,908,447 A | 6/1999 | Schroeppel et al. |
| 6,041,258 A | 3/2000 | Cigaina et al. |
| 6,055,457 A | 4/2000 | Bonner |
| 6,074,401 A | 6/2000 | Gardnier et al. |
| 6,078,840 A | 6/2000 | Stokes |
| 6,093,177 A | 7/2000 | Javier et al. |
| 6,129,749 A | 10/2000 | Bartig et al. |
| 6,132,456 A | 10/2000 | Sommer et al. |
| 6,181,973 B1 | 1/2001 | Ceron et al. |
| 6,188,932 B1 | 2/2001 | Lindegren |
| 6,240,322 B1 | 5/2001 | Peterfeso et al. |
| 6,251,104 B1 | 6/2001 | Kesten et al. |
| 6,290,719 B1 | 9/2001 | Garberoglio |
| 6,321,124 B1 | 11/2001 | Cigaina |
| 6,322,548 B1 | 11/2001 | Payne et al. |
| RE37,463 E | 12/2001 | Altman |
| 6,358,256 B1 | 3/2002 | Reinhardt |
| 6,363,938 B2 | 4/2002 | Saadat et al. |
| 6,381,495 B1 | 4/2002 | Jenkins |
| 6,381,500 B1 | 4/2002 | Fischer, Sr. |
| 6,408,214 B1 | 6/2002 | Williams et al. |
| 6,458,145 B1 | 10/2002 | Ravenscroft et al. |
| 6,477,423 B1 | 11/2002 | Jenkins |
| 6,500,182 B2 | 12/2002 | Foster |
| 6,508,803 B1 | 1/2003 | Horikawa et al. |
| 6,510,332 B1 | 1/2003 | Greenstein |
| 6,510,345 B1 | 1/2003 | Van Bentem |
| 6,522,915 B1 | 2/2003 | Ceballos et al. |
| 6,572,587 B2 | 6/2003 | Lerman et al. |
| 6,582,441 B1 | 6/2003 | He et al. |
| 6,592,581 B2 | 7/2003 | Bowe |
| 6,623,518 B2 | 9/2003 | Thompson et al. |
| 6,626,915 B2 | 9/2003 | Leveillee |
| 6,638,268 B2 | 10/2003 | Niazi |
| 6,684,109 B1 | 1/2004 | Osypka |
| 6,711,443 B2 | 3/2004 | Osypka |
| 6,743,240 B2 | 6/2004 | Smith et al. |
| 6,755,812 B2 | 6/2004 | Peterson et al. |
| 6,909,920 B2 | 6/2005 | Lokhoff et al. |
| 6,944,507 B2 | 9/2005 | Froberg et al. |
| 6,953,454 B2 | 10/2005 | Peterson et al. |
| 7,027,876 B2 | 4/2006 | Casavant et al. |
| 7,082,335 B2 | 7/2006 | Klein et al. |
| 7,085,606 B2 | 8/2006 | Flach et al. |
| 7,092,765 B2 | 8/2006 | Geske et al. |
| 7,092,766 B1 | 8/2006 | Salys et al. |
| 7,120,504 B2 | 10/2006 | Osypka |
| 7,149,587 B2 | 12/2006 | Wardle et al. |
| 7,158,838 B2 | 1/2007 | Seifert et al. |
| 7,162,310 B2 | 1/2007 | Doan |
| 7,181,288 B1 | 2/2007 | Rezai et al. |
| 7,187,982 B2 | 3/2007 | Seifert et al. |
| 7,200,437 B1 | 4/2007 | Nabutovsky et al. |
| 7,212,869 B2 | 5/2007 | Wahlstrom et al. |
| 7,229,415 B2 | 6/2007 | Schwartz |
| 7,251,532 B2 | 7/2007 | Hess et al. |
| 7,289,853 B1 | 10/2007 | Campbell et al. |
| 7,313,445 B2 | 12/2007 | McVenes et al. |
| 7,326,231 B2 | 2/2008 | Phillips et al. |
| 7,328,071 B1 | 2/2008 | Stehr et al. |
| 7,383,091 B1 | 6/2008 | Chitre et al. |
| 7,450,999 B1 | 11/2008 | Karicherla et al. |
| 7,462,184 B2 | 12/2008 | Worley et al. |
| 7,463,933 B2 | 12/2008 | Wahlstrom et al. |
| 7,499,758 B2 | 3/2009 | Cates et al. |
| 7,509,169 B2 | 3/2009 | Eigler et al. |
| 7,515,971 B1 | 4/2009 | Doan |
| 7,532,939 B2 | 5/2009 | Sommer et al. |

(56) References Cited

U.S. PATENT DOCUMENTS

| | | | |
|---|---|---|---|
| 7,558,631 B2 | 7/2009 | Cowan et al. |
| 7,634,319 B2 | 12/2009 | Schneider et al. |
| 7,647,109 B2 | 1/2010 | Hastings et al. |
| 7,657,325 B2 | 2/2010 | Williams |
| 7,678,128 B2 | 3/2010 | Boyle et al. |
| 7,717,899 B2 | 5/2010 | Bowe et al. |
| 7,731,655 B2 | 6/2010 | Smith et al. |
| 7,734,343 B2 | 6/2010 | Ransbury et al. |
| 7,740,640 B2 | 6/2010 | Ginn |
| 7,785,264 B2 | 8/2010 | Hettrick et al. |
| 7,799,037 B1 | 9/2010 | He et al. |
| 7,801,624 B1 | 9/2010 | Flannery et al. |
| 7,835,801 B1 | 11/2010 | Sundararajan et al. |
| 7,840,281 B2 | 11/2010 | Kveen et al. |
| 7,840,283 B1 | 11/2010 | Bush et al. |
| 7,860,580 B2 | 12/2010 | Falk et al. |
| 7,875,049 B2 | 1/2011 | Eversull et al. |
| 7,890,186 B2 | 2/2011 | Wardle et al. |
| 7,904,179 B2 | 3/2011 | Rutten et al. |
| 7,920,928 B1 | 4/2011 | Yang et al. |
| 7,993,351 B2 | 8/2011 | Worley et al. |
| 8,010,209 B2 | 8/2011 | Jacobson |
| 8,012,143 B1 | 9/2011 | Kampa |
| 8,036,757 B2 | 10/2011 | Worley |
| 8,057,486 B2 | 11/2011 | Hansen |
| 8,082,035 B2 | 12/2011 | Glukhovsky |
| 8,103,361 B2 | 1/2012 | Moser |
| 8,108,054 B2 | 1/2012 | Helland |
| 8,142,347 B2 | 3/2012 | Griego et al. |
| 8,160,722 B2 | 4/2012 | Rutten et al. |
| 8,185,213 B2 | 5/2012 | Kveen et al. |
| 8,219,213 B2 | 7/2012 | Sommer et al. |
| 8,233,994 B2 | 7/2012 | Sommer et al. |
| 8,252,019 B2 | 8/2012 | Fleming, III |
| 8,295,939 B2 | 10/2012 | Jacobson |
| 8,313,445 B2 | 11/2012 | Mishima et al. |
| 8,352,025 B2 | 1/2013 | Jacobson |
| 8,352,028 B2 | 1/2013 | Wenger |
| 8,364,277 B2 | 1/2013 | Glukhovsky |
| 8,364,280 B2 | 1/2013 | Marnfeldt et al. |
| 8,406,900 B2 | 3/2013 | Barlov et al. |
| 8,406,901 B2 | 3/2013 | Starkebaum et al. |
| 8,428,750 B2 | 4/2013 | Kolberg |
| 8,452,420 B2 | 5/2013 | Flach et al. |
| 8,478,431 B2 | 7/2013 | Griswold et al. |
| 8,489,189 B2 | 7/2013 | Tronnes |
| 8,494,650 B2 | 7/2013 | Glukhovsky et al. |
| 8,504,156 B2 | 8/2013 | Bonner et al. |
| 8,518,060 B2 | 8/2013 | Jelich et al. |
| 8,527,068 B2 | 9/2013 | Ostroff |
| 8,532,790 B2 | 9/2013 | Griswold |
| 8,548,605 B2 | 10/2013 | Ollivier |
| 8,565,897 B2 | 10/2013 | Regnier et al. |
| 8,615,310 B2 | 12/2013 | Khairkhahan et al. |
| 8,634,912 B2 | 1/2014 | Bornzin et al. |
| 8,670,842 B1 | 3/2014 | Bornzin et al. |
| 8,721,587 B2 | 5/2014 | Berthiaume et al. |
| 8,727,996 B2 | 5/2014 | Allan et al. |
| 8,758,365 B2 | 6/2014 | Bonner et al. |
| 10,265,503 B2 * | 4/2019 | Schmidt ............ A61M 25/0082 |
| 2002/0077556 A1 | 6/2002 | Schwartz |
| 2003/0004537 A1 | 1/2003 | Boyle et al. |
| 2003/0078618 A1 * | 4/2003 | Fey ...................... A61B 5/6882 |
| | | 607/2 |
| 2003/0216642 A1 | 11/2003 | Pepin et al. |
| 2004/0176797 A1 | 9/2004 | Opolski |
| 2005/0090890 A1 | 4/2005 | Wu et al. |
| 2005/0267555 A1 | 12/2005 | Marnfeldt et al. |
| 2006/0100640 A1 | 5/2006 | Bolduc |
| 2006/0247720 A1 | 11/2006 | Starkebaum |
| 2006/0247753 A1 | 11/2006 | Wenger et al. |
| 2007/0135883 A1 | 6/2007 | Drasler et al. |
| 2007/0150037 A1 | 6/2007 | Hastings et al. |
| 2007/0150038 A1 | 6/2007 | Hastings et al. |
| 2007/0233218 A1 | 10/2007 | Kolberg |
| 2007/0239248 A1 | 10/2007 | Hastings et al. |
| 2007/0255376 A1 | 11/2007 | Michels et al. |
| 2007/0276444 A1 | 11/2007 | Gelbart |
| 2007/0293904 A1 | 12/2007 | Gelbart |
| 2008/0021532 A1 | 1/2008 | Kveen et al. |
| 2008/0283066 A1 | 11/2008 | Delgado et al. |
| 2009/0082828 A1 | 3/2009 | Ostroff |
| 2009/0281605 A1 | 11/2009 | Marnfeldt et al. |
| 2010/0198288 A1 | 8/2010 | Ostroff |
| 2010/0321968 A1 | 12/2010 | Jones et al. |
| 2011/0034939 A1 | 2/2011 | Kveen et al. |
| 2011/0112548 A1 | 5/2011 | Fifer et al. |
| 2011/0125163 A1 | 5/2011 | Rutten et al. |
| 2011/0190785 A1 | 8/2011 | Gerber et al. |
| 2011/0190786 A1 | 8/2011 | Gerber et al. |
| 2011/0208260 A1 | 8/2011 | Jacobson |
| 2011/0237967 A1 | 9/2011 | Moore et al. |
| 2011/0270339 A1 | 11/2011 | Murray, III et al. |
| 2011/0270340 A1 | 11/2011 | Pellegrini et al. |
| 2011/0282423 A1 | 11/2011 | Jacobson |
| 2011/0307043 A1 | 12/2011 | Ollivier |
| 2012/0078322 A1 | 3/2012 | Dal Molin et al. |
| 2012/0078336 A1 | 3/2012 | Helland |
| 2012/0095539 A1 | 4/2012 | Khairkhahan et al. |
| 2012/0109002 A1 | 5/2012 | Mothilal et al. |
| 2012/0109079 A1 | 5/2012 | Asleson et al. |
| 2012/0109148 A1 | 5/2012 | Bonner et al. |
| 2012/0109149 A1 | 5/2012 | Bonner et al. |
| 2012/0116489 A1 | 5/2012 | Khairkhahan et al. |
| 2012/0158111 A1 | 6/2012 | Khairkhahan et al. |
| 2012/0165827 A1 | 6/2012 | Khairkhahan et al. |
| 2012/0172690 A1 | 7/2012 | Anderson et al. |
| 2012/0172891 A1 | 7/2012 | Lee |
| 2012/0172892 A1 | 7/2012 | Grubac et al. |
| 2012/0197373 A1 | 8/2012 | Khairkhahan et al. |
| 2012/0232565 A1 | 9/2012 | Kveen et al. |
| 2012/0271134 A1 | 10/2012 | Allan et al. |
| 2012/0330392 A1 | 12/2012 | Regnier et al. |
| 2013/0006261 A1 | 1/2013 | Lampropoulos et al. |
| 2013/0006262 A1 | 1/2013 | Lampropoulos et al. |
| 2013/0012925 A1 | 1/2013 | Berthiaume et al. |
| 2013/0035636 A1 | 2/2013 | Beasley et al. |
| 2013/0035748 A1 | 2/2013 | Bonner et al. |
| 2013/0053921 A1 | 2/2013 | Bonner et al. |
| 2013/0079798 A1 | 3/2013 | Tran et al. |
| 2013/0079861 A1 | 3/2013 | Reinert et al. |
| 2013/0103047 A1 | 4/2013 | Steingisser et al. |
| 2013/0103049 A1 | 4/2013 | Medtronic |
| 2013/0116741 A1 | 5/2013 | Bornzin et al. |
| 2013/0123875 A1 | 5/2013 | Varady et al. |
| 2013/0131591 A1 | 5/2013 | Berthiaume et al. |
| 2013/0131693 A1 | 5/2013 | Berthiaume et al. |
| 2013/0253342 A1 | 9/2013 | Griswold et al. |
| 2013/0253343 A1 | 9/2013 | Waldhauser et al. |
| 2013/0253344 A1 | 9/2013 | Griswold et al. |
| 2013/0253345 A1 | 9/2013 | Griswold et al. |
| 2013/0253346 A1 | 9/2013 | Griswold et al. |
| 2013/0253347 A1 | 9/2013 | Griswold et al. |
| 2013/0296957 A1 | 11/2013 | Tronnes |
| 2014/0058494 A1 | 2/2014 | Ostroff et al. |
| 2014/0074114 A1 | 3/2014 | Khairkhahan et al. |
| 2014/0148815 A1 | 5/2014 | Wenzel et al. |
| 2014/0180306 A1 | 6/2014 | Grubac et al. |

FOREIGN PATENT DOCUMENTS

| | | | |
|---|---|---|---|
| EP | 779080 B1 | 5/2003 |
| JP | 05245215 A | 9/1993 |
| WO | 03032807 A2 | 4/2003 |
| WO | 2009039400 A1 | 3/2009 |
| WO | 2012092067 A1 | 7/2012 |
| WO | 2012092074 A1 | 7/2012 |

\* cited by examiner

DELIVERY DEVICES AND METHODS FOR LEADLESS CARDIAC DEVICES

CROSS-REFERENCES TO RELATED APPLICATIONS

This application is a continuation application of U.S. application Ser. No. 14/452,654, filed Aug. 6, 2014, which claims the benefit of priority under 35 U.S.C. § 119(e) of U.S. Provisional Application No. 61/866,715 filed Aug. 16, 2013, the complete disclosure of which are herein incorporated by reference in their entirety

TECHNICAL FIELD

The present disclosure pertains to medical devices, and methods for manufacturing and/or using medical devices. More particularly, the present disclosure pertains to leadless cardiac devices and methods, such as leadless pacing devices and methods, and delivery devices and methods for such leadless devices.

BACKGROUND

A wide variety of medical devices have been developed for medical use, for example, cardiac use. Some of these devices include catheters, leads, pacemakers, and the like, and delivery devices and/or systems used for delivering such devices. These devices are manufactured by any one of a variety of different manufacturing methods and may be used according to any one of a variety of methods. Of the known medical devices, delivery system, and methods, each has certain advantages and disadvantages. There is an ongoing need to provide alternative medical devices and delivery devices as well as alternative methods for manufacturing and using medical devices and delivery devices.

BRIEF SUMMARY

This disclosure provides design, material, manufacturing method, and use alternatives for medical devices, including delivery devices. An example medical device includes a delivery device for delivering an implantable leadless pacing device. The delivery device may include a proximal section including a first deflection mechanism, and a distal holding section extending distally of a distal end of the proximal section. The distal holding section may define a cavity therein for receiving an implantable leadless pacing device. In some embodiments, the proximal section includes a second deflection mechanism, such as two or more deflection mechanisms.

The distal holding section may be configured to slidably receive the implantable leadless pacing device, and in some cases the distal holding section is designed to receive a non-expandable, implantable leadless pacing device. In some embodiments, the proximal section defines a lumen, and a push member is disposed within the lumen, and the push member is designed to push the implantable leadless pacing device out of the distal holding section.

In some embodiments, the proximal section of the delivery device may include an outer tubular member and an inner tubular member, and in some cases the outer and inner tubular members are axially translatable relative to each other. In some cases the inner tubular member, the outer tubular member, or both include a deflection mechanism. In some cases, each the inner and outer tubular members, or both may include two or more deflection mechanisms.

In some embodiments, the proximal section of the delivery device includes a portion having one or more fixed curve. In some cases the proximal section may include an outer tubular member, an inner tubular member, or both that may include one or more fixed curve.

The outer diameter of the proximal section may be less than an outer diameter of the distal holding section. In some cases, the distal end of an inner tubular member is connected to a proximal end of the distal holding section, and wherein an outer diameter of the distal holding section is greater than an outer diameter of the inner tubular member. In some cases, at least a portion of the inner tubular member is disposed within an outer tubular member, and wherein the outer tubular member has an inner diameter that is less than the outer diameter of the distal holding section.

In some cases, the distal holding section includes a distal tip portion and a body portion. The distal tip portion may be deformable to provide an atraumatic surface for engagement with a tissue of a patient. In some cases, the tip portion comprises a softer material than a material of at least a portion of the body portion. In some cases, the tip portion comprises a polymer having a durometer less than that of at least a portion of the body portion. The distal tip portion may include a wall thickness that is greater than a wall thickness of at least a portion of the body portion. The distal tip portion may include a rounded distal end. In some cases, the distal tip portion includes an angled distal end surface that defines an acute angle relative to a longitudinal axis of the distal holding section, and the angled distal end surface may be configured to flatten against a tissue surface of a patient when brought into contact with the tissue surface.

In some embodiments, the distal holding section includes an inner layer defining an inner surface, and an outer layer, wherein the inner layer comprises a polymer having a durometer greater than that of at least a portion of the outer layer.

In some embodiments, the distal holding section includes a wall defining a cavity for receiving the implantable leadless pacing device, and one or more conductive pathways are defined in the wall that are spaced proximally from a distal end of the distal holding section. In some cases, the one or more conductive pathways includes one or more openings defined in the wall that allow for fluid communication therethrough of a conductive fluid. In some embodiments, the one or more conductive pathways includes one or more sections defined in the wall that comprise a conductive material.

Some embodiments relate to an implantable leadless pacing device system including any of the elements or combination of elements of delivery devices described above, or herein, in combination with an implantable leadless pacing device received within a distal holding section of the delivery device.

Some additional embodiments relate to a method for delivering an implantable leadless pacing device. Some such methods include delivering the implantable leadless pacing device into the heart of a patient using a delivery system or delivery device including any of the elements or combination of elements of delivery systems or delivery devices as described above or herein.

The above summary of some embodiments is not intended to describe each disclosed embodiment or every implementation of the present disclosure. The Figures, and Detailed Description, which follow, more particularly exemplify some of these embodiments.

BRIEF DESCRIPTION OF THE DRAWINGS

The disclosure may be more completely understood in consideration of the following detailed description in connection with the accompanying drawings, in which.

Figure 1:
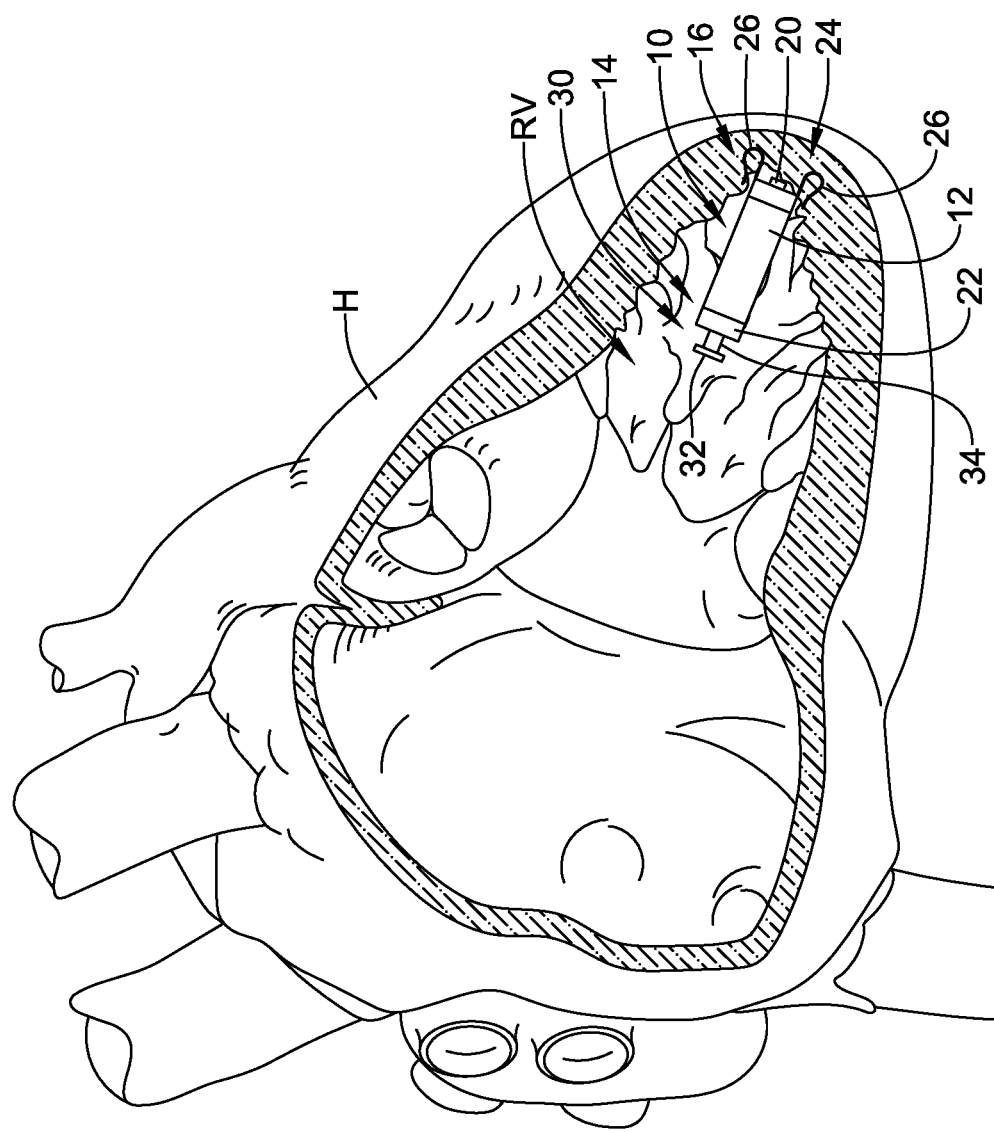
FIG. 1 is a plan view of an example leadless pacing device implanted within a heart.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar structures in different drawings are numbered the same. The drawings, which are not necessarily to scale, depict illustrative embodiments and are not intended to limit the scope of the disclosure.

Cardiac pacemakers provide electrical stimulation to heart tissue to cause the heart to contract and thus pump blood through the vascular system. Conventional pacemakers typically include an electrical lead that extends from a pulse generator implanted subcutaneously or sub-muscularly to an electrode positioned adjacent the inside or outside wall of the cardiac chamber. As an alternative to conventional pacemakers, self-contained or leadless cardiac pacemakers have been proposed. Leadless cardiac pacemakers are small capsules typically fixed to an intracardiac implant site in a cardiac chamber. The small capsule typically includes bipolar pacing/sensing electrodes, a power source (e.g. a battery), and associated electrical circuitry for controlling the pacing/sensing electrodes, and thus provide electrical stimulation to heart tissue and/or sense a physiological condition. It can be readily appreciated that the implantation of a leadless pacing device within a beating heart could become dislodged as the heart functions. Accordingly, it may be desirable for a leadless pacing device to include one or more anchoring mechanism or member to help securing the pacing device to the heart.

FIG. 1 illustrates an example implantable leadless cardiac pacing device 10 (e.g., a leadless pacemaker) is illustrated implanted in a chamber of a heart H, such as the right ventricle RV. The implantable device 10 may include a shell or housing 12 having a proximal end 14 and a distal end 16. The implantable device 10 may include a first electrode 20 positioned adjacent to the distal end 16 of the housing 12 and a second electrode 22 positioned adjacent to the proximal end 14 of the housing 12. For example, housing 12 may include a conductive material and may be insulated along a portion of its length. A section along proximal end 14 may be free of insulation so as to define second electrode 22. The electrodes 20, 22 may be sensing and/or pacing electrodes to provide electro-therapy and/or sensing capabilities. The first electrode 20 may be capable of being positioned against or otherwise contact the cardiac tissue of the heart H while the second electrode 22 may be spaced away from the first electrode 20, and thus spaced away from the cardiac tissue.

The implantable device 10 may include a pulse generator (e.g., electrical circuitry) and a power source (e.g., a battery) within the housing 12 to provide electrical signals to the electrodes 20, 22 and thus control the pacing/sensing electrodes 20, 22. Electrical communication between pulse generator and the electrodes 20, 22 may provide electrical stimulation to heart tissue and/or sense a physiological condition.

The implantable device 10 may include a fixation mechanism 24 proximate the distal end 16 of the housing 12 configured to attach the implantable device 10 to a tissue wall of the heart H, or otherwise anchor the implantable device 10 to the anatomy of the patient. As shown in FIG. 1, in some instances, the fixation mechanism 24 may include one or more, or a plurality of hooks 26 anchored into the cardiac tissue of the heart H to attach the implantable device 10 to a tissue wall. In other instances, the fixation mechanism 24 may include one or more, or a plurality of passive tines, configured to entangle with trabeculae within the chamber of the heart H and/or a helical fixation anchor configured to be screwed into a tissue wall to anchor the implantable device 10 to the heart H.

The implantable device 10 may include a docking member 30 proximate the proximal end 14 of the housing 12 configured to facilitate delivery and/or retrieval of the implantable device 10. For example, the docking member 30 may extend from the proximal end 14 of the housing 12 along a longitudinal axis of the housing 12. The docking member 30 may include a head portion 32 and a neck portion 34 extending between the housing 12 and the head portion 32. The head portion 32 may be an enlarged portion relative to the neck portion 34. For example, the head portion 32 may have a radial dimension from the longitudinal axis of the implantable device 10 which is greater than a radial dimension of the neck portion from the longitudinal axis of the implantable device 10. The docking member 30 may be configured to facilitate delivery of the implantable device 10 to the intracardiac site and/or retrieval of the implantable device 10 from the intracardiac site. Other docking members 30 are contemplated.

One aspect of the current disclosure relates to the delivery device and/or system used, for example, to deliver device 10 to a suitable location within the anatomy (e.g., the heart). As may be appreciated, the delivery device may need to be navigated through relatively tortuous anatomy to deliver the device 10 to a suitable location. For instance, in some embodiments, the delivery device may be advanced through the vasculature to a target region. In some example cases the device may be advanced through a femoral vein, into the inferior vena cava, into the right atrium, through the tricuspid valve, and into the right ventricle. The target region for the delivery of the device 10 may be a portion of the right ventricle, for example, a portion of the right ventricle near the apex of the heart. The target region may also include other regions of the heart (e.g., right atrium, left atrium, or left ventricle), blood vessels, or other suitable targets. It may be desirable to provide the delivery system with certain features that may allow for easier or better control for navigation or delivery purposes.

Figure 2:
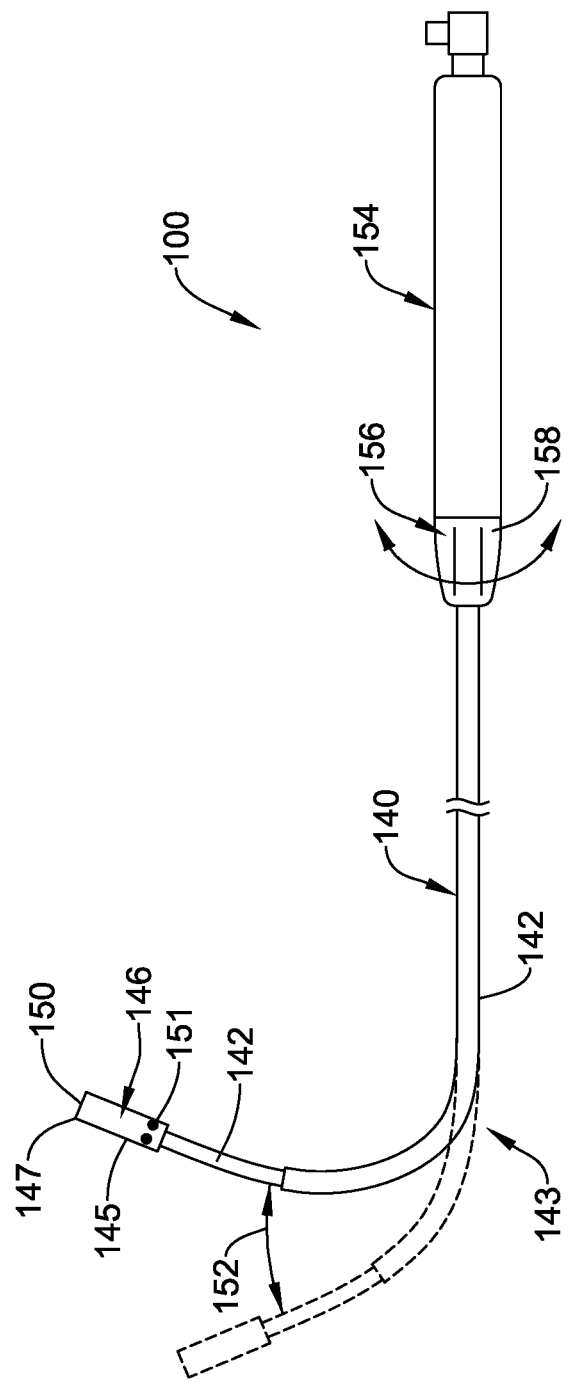
FIG. 2 is a side view of an example delivery device for an implantable leadless cardiac pacing device.
Figure 2A:
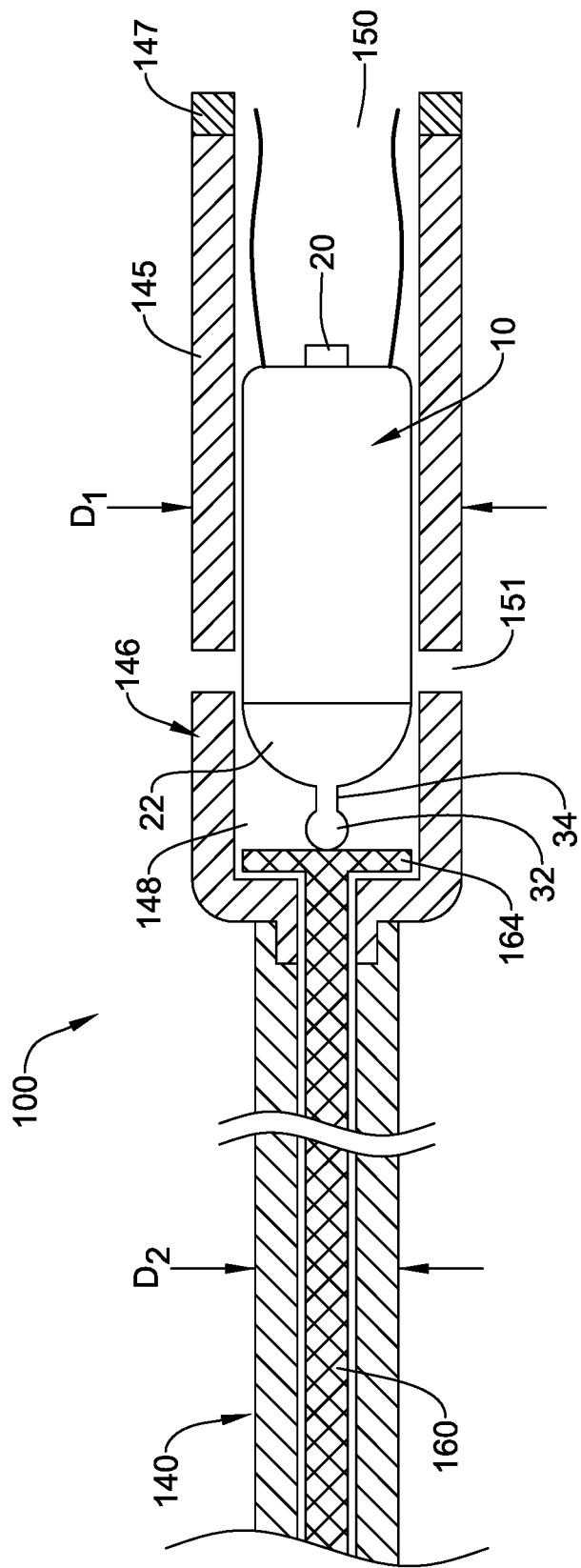
FIG. 2A is a partial cross-sectional side view of the distal portion of the delivery device of FIG. 2, showing the implantable leadless cardiac pacing device disposed therein.

FIGS. 2 and 2A illustrate an example embodiment of a delivery device 200, such as catheter, that may be used to deliver the device 10. Delivery device 100 may include a proximal section 140, such as a proximal shaft, and a distal section and/or holding section 146, attached to the distal end of the proximal section 140. The delivery device 100 may also include a proximal hub portion 154 attached to the proximal end of the proximal section 140. In some embodiments, the proximal section 140 may include at least a section thereof that has an outer diameter D2 that is less than the outer diameter D1 of at least a portion of the holding section 146. (see e.g. FIG. 2A).

The distal holding section 146 may be configured to receive the implantable device 10 therein. For example, referring to both FIGS. 2 and 2A, the holding section 146 may define a cavity 148 for slidably receiving the implantable device 10, and may include a distal opening 150 for slidable insertion and/or extraction of the implantable device 10 into and/or out of the cavity 148.

The distal holding section 146 may include a body portion 145 and a distal tip portion 147 that may be, for example, configured to be atraumatic to anatomy, such as a bumper tip. For example, as the catheter is navigated through the anatomy, the distal tip may come into contact with anatomy. Additionally, when the catheter is used to deliver the device, the tip 147 of the delivery device 100 will likely come into contact with tissue adjacent the target cite (e.g. cardiac tissue of the heart). A hard distal tip formed of the material of the elongate proximal section 140 may injure a vessel wall or cardiac tissue. As such, it may be desirable to provide the delivery device 100 with a softer distal tip that can be introduced into the anatomy and come into contact with anatomy adjacent the target cite without causing unnecessary trauma.

For example, the distal tip 147 may be made of a material that is softer than the body portion 145 of the distal holding section. In some cases, the distal tip 147 may include a material that has a durometer that is less than the durometer of the material of the body portion 145. In some particular embodiments, the durometer of the material used in the distal tip may be in the range of about 5 D to about 70 D, or for example, in the range of about 25 D to about 65 D. Additionally, the distal tip may include a shape or structure that may make it less traumatic to tissue. For example, the distal tip may have a distal surface, such as a tissue contacting surface, that is that is rounded or includes a curvature configured to be more atraumatic to tissue.

In some embodiments, all or a portion of the distal holding section 146 may include an inner surface that may be configured to resist getting caught on the fixation mechanism 24, such as the one or more, or a plurality of hooks 26 on the device 10. For example, the distal holding section 146 may include an inner layer or coating of harder or more lubricious material that resists force applied by the fixation mechanism 24 onto the inner surface of the distal holding section 146. For example, the distal holding section 146 may include a multi-layered structure, and an inner layer may be made of a material that is harder than an outer layer.

The distal holding section 146 may also define one or more conductive pathways 151 that are spaced proximally from the distal opening 150 in the distal end of the distal holding section. For example, the conductive pathways 151 may include one or more opening the wall of the distal holding section 146 that allow for fluid communication there through of a conductive fluid, such as blood. Such a conductive pathway may allow for conductive communication between electrodes 20, 22 on the device 10 through the distal opening 150 and the pathway openings 151 respectively, while the device is housed within the cavity 148. Such communication may allow the device 10 to be tested prior to being released or delivered out of the cavity 148. Other conductive pathways are also contemplated. For example, the one or more conductive pathways may include one or more sections defined in the wall of the distal holding section 146 that comprises a conductive material, such as conductive metals, polymers, and the like. In at least some embodiments, the distal holding section 146 may be free of the conductive pathways 151.

A push member 160 may be disposed (e.g., slidably disposed) within a lumen of the delivery device 100. The push member 160 may be engaged by a user near the proximal end of the delivery device 100, and extend through a lumen in the delivery device 100, through the proximal section 140 and into the distal holding section 146. A distal portion 164 of the push member 160 may be capable of engaging the device 10, and the push member 160 may be used to "push" device 10 out from distal holding section 146 so as to deploy and anchor device 10 within a target region (e.g., a region of the heart such as the right ventricle).

In order to more specifically place or steer delivery device 100 to a position adjacent to the intended target, delivery device 100 may be configured to be deflectable or articulable or steerable. Referring to FIG. 2, for example, the proximal section 140 may include one or more articulation or deflection mechanism(s) that may allow for the catheter 100, or portions thereof, to be deflected, articulated, steered and/or controlled in a desired manner. For example, the proximal section 140 may include a shaft, such as a tubular shaft member 142 that includes at least a portion thereof that can be selectively bent and/or deflected in a desired or predetermined direction. This may, for example, allow a user to orient the delivery device 100 such that the holding section 146 is in a desirable position or orientation for navigation or delivery of the device 10 to a target location. As shown in FIG. 2, the shaft member 142 may be deflected, for example, along deflection region 143 from a first example position indicated in phantom lines, to a second example position indicated in solid lines along a deflection path 152.

A wide variety of deflection mechanisms may be used. In some example embodiments, deflection may be effected by one or more actuation members, such as pull wire(s) extending between a distal portion of the catheter shaft member 142 and an actuation mechanism 156 near the proximal end of the shaft member 142. As such, the one or more pull wires may extend both proximally and distally of the desired deflection or bending region or point. This allows a user to actuate (e.g., "pull") one or more of the pull wires to apply a compression and/or deflection force to at least a portion of the shaft 142 and thereby deflect or bend the shaft member 142 in a desired manner. In addition, in some cases the one or more wires may be stiff enough so that they can also be used to provide a pushing and/or tensioning force on the shaft member 142, for example, to "push" or "straighten" the shaft into a desired position or orientation.

In some embodiments, the actuation member takes the form of a continuous wire that is looped through or otherwise coupled to a distal end of the shaft member 142 so as to define a pair of wire sections. Other embodiments are contemplated, however, including embodiments where the actuation member includes one or a plurality of individual wires that are attached, for example, to the distal end of the shaft member 142.

The actuation mechanism 156 may include a desired mechanism that may allow for applying tension (i.e. pulling force), or compression (i.e. pushing force), or both, on the actuation member(s). In some embodiments, the actuation mechanism 156 may include an external rotatable member 158 connected to and rotatable about the longitudinal axis of the hub 154. The rotatable member 158 may threadingly engage an internal member that is attached to the proximal end of the actuation member(s) or pull wires. When the external rotatable member 158 is rotated in a first rotational direction, the internal member translates in a first longitudinal direction, thereby applying tension to the pull wires, which applies compression force to the shaft, so as to deflect the shaft member 142 from an initial position to a deflected position. When the external rotatable member 158 is rotated in a second rotational direction, the internal member translates in a second longitudinal direction, thereby releasing the tension on the pull wires, and allowing the shaft member 142 to relax back toward the initial position. Additionally, in some cases, as mentioned above, where the one or more wires may be stiff enough, rotation of the rotatable member 158 in the second rotational direction such that the internal member translates in a second longitudinal direction may apply compression to the wires, such that the wires may apply tension to the shaft member 142 and "push" the shaft member 142 back toward an initial position, and possibly into additional positions beyond the initial position.

The one or more articulation and/or deflection mechanism(s) may also entail the shaft member 142 including structure and/or material that may provide for the desired degree and/or location of the deflection when the compressive or tensile forces are applied. For example, the shaft member 142 may include one or more sections that include structure and/or material configured to allow the shaft to bend and/or deflect in a certain way when a certain predetermined compressive and/or tensile force is applied. For example, the shaft may include one or more sections that are more flexible than other sections, thereby defining a bending or articulating region or location. Some such regions may include a number of varying or changing flexibility characteristics that may define certain bending shapes when predetermined forces are applied. Such characteristics may be achieved through the selection of materials or structure for different sections of the shaft member 142.

In other embodiments, other articulation and/or deflection mechanism(s) are contemplated. For example, all or a portion of the delivery device 100, such as the proximal section 140, such as shaft member 142, may be made of a shape memory material, such as a shape memory polymer and/or a shape memory metal. Such materials, when stimulated by an actuation mechanism, such as a change in temperature or the application of an electrical current, may change or move from a first shape to a second shape. As such, these material and mechanism may be used to deflect or bend the shaft member 142 in a desired manner. Other suitable deflection mechanism(s) that are able to deflect the delivery device 100 may also be used. Such alternative mechanisms may be applied to all other embodiments shown and/or discussed herein, and others, as appropriate.

Furthermore, the shaft member 142 may include one or more predefined or fixed curve portion(s) along the length thereof. In some cases, such curved sections may be configured to fit with particular anatomies or be configured for better navigation or delivery of the device 10. Additionally, or alternatively, some such curved sections may be configured to allow the shaft member 142 to be predisposed to be bent and/or deflected in a certain direction or configuration when compression and/or tension forces are applied thereto.

Figure 3:
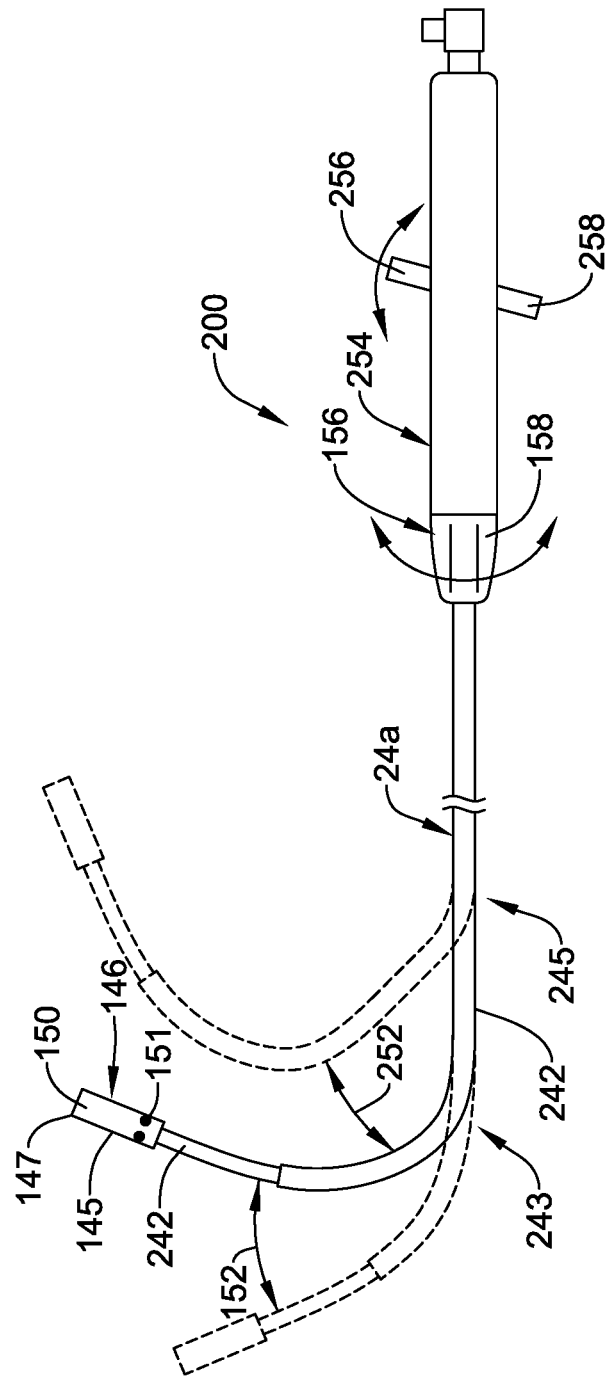
FIG. 3 is a side view of another example delivery device for an implantable leadless cardiac pacing device.

FIG. 3 shows another example embodiment of a delivery device 200, such as a catheter, which is similar in many respects to that of the delivery device 100 shown in FIG. 2, with similar structures numbered the same. The delivery device 200 in this embodiment includes two articulation and/or deflection mechanism(s). For example, the proximal section 240 may include a shaft, such as a tubular shaft member 242 that includes at least two portions thereof that can be selectively bent and/or deflected in desired or predetermined directions. Again, this may allow a user to orient the catheter 200 such that the holding section 146 is in a desirable position or orientation for navigation or delivery of the device 10 to a target location.

As shown in FIG. 3, the shaft member 242 may be deflected along deflection region 243 to various desirable positions, for example from a first position indicated in phantom lines, to a second position indicated in solid lines along a deflection path 152. Further, the shaft member 242 may be deflected along deflection region 245 to various desirable positions, for example, from a third position shown in solid lines to a fourth position shown in phantom lines along deflection path 252. The two articulation and/or deflection mechanism(s) allow for compound deflection of the shaft 242, which may allow for better maneuverability or positioning of the shaft 242 as desired. The deflection along the two deflection paths 152 and 252 may extend in the same plane, or alternatively, may allow for deflection or articulation of the shaft 242 in planes that are offset from one another.

Hub 254 may include one or more actuation mechanism for controlling the desired degree of deflection along one or both of the deflection regions 243 and 245. For example, two separate actuation mechanisms may be used—one for controlling deflection along each of the deflection regions 243 and 245. However, it is contemplated that in other embodiments, a single actuation mechanism may be used to control deflection along both deflection regions 243 and 245.

An appropriate actuation mechanism may be used, for example, such any of those discussed above or relative to the embodiment shown in FIG. 2. In the embodiment shown in FIG. 3, the hub includes an actuation mechanism 156 that is similar to that discussed above relative to the embodiment shown in FIG. 2, which may be used for example, to control deflection along deflection regions 243.

Furthermore, the hub 254 includes a second actuation mechanism 256 that may be used, for example, to control deflection along deflection region 245. The actuation mechanism 256 is shown as a toggle mechanism that may be used in conjunction with one or more actuation members, such as pull wire(s), as discussed above, that are configured to effect deflection along deflection region 245 when appropriate compressive and/or tensile forces are applied thereto. The toggle actuation mechanism 256 may include a lever member 258 connected for pivotal movement relative to the hub 254. The lever member 258 may be attached to the proximal end of the pull wire(s) for deflection region 245. When the lever member 258 is pivoted in a first direction, it applies tension to the pull wire(s), which applies compression force to the shaft, so as to deflect the shaft 242 along deflection region 245, for example, along path 252 from the third position to the fourth position. When the lever member 258 is pivoted in a second direction, it releases the tension on the pull wire(s) and allows the shaft 242 to relax back toward the initial position. Additionally, in some cases, as mentioned above, where the one or more wires may be stiff enough, pivoting the lever member 258 in a second direction may apply compression to the wires, such that the wires may apply tension to the shaft 242 and "push" the shaft back toward an initial position, and possibly into additional positions beyond the initial position.

The shaft member 242 may include similar structure and materials as discussed above regarding the embodiment shown in FIG. 2, including one or more predefined or fixed curve portion(s) along the length thereof. Furthermore, while this embodiment shows two deflection mechanism or deflection regions, more than two are contemplated. For example, three or more deflection mechanism or deflection regions or deflection paths may be incorporated into other embodiments as desired.

Figure 4:
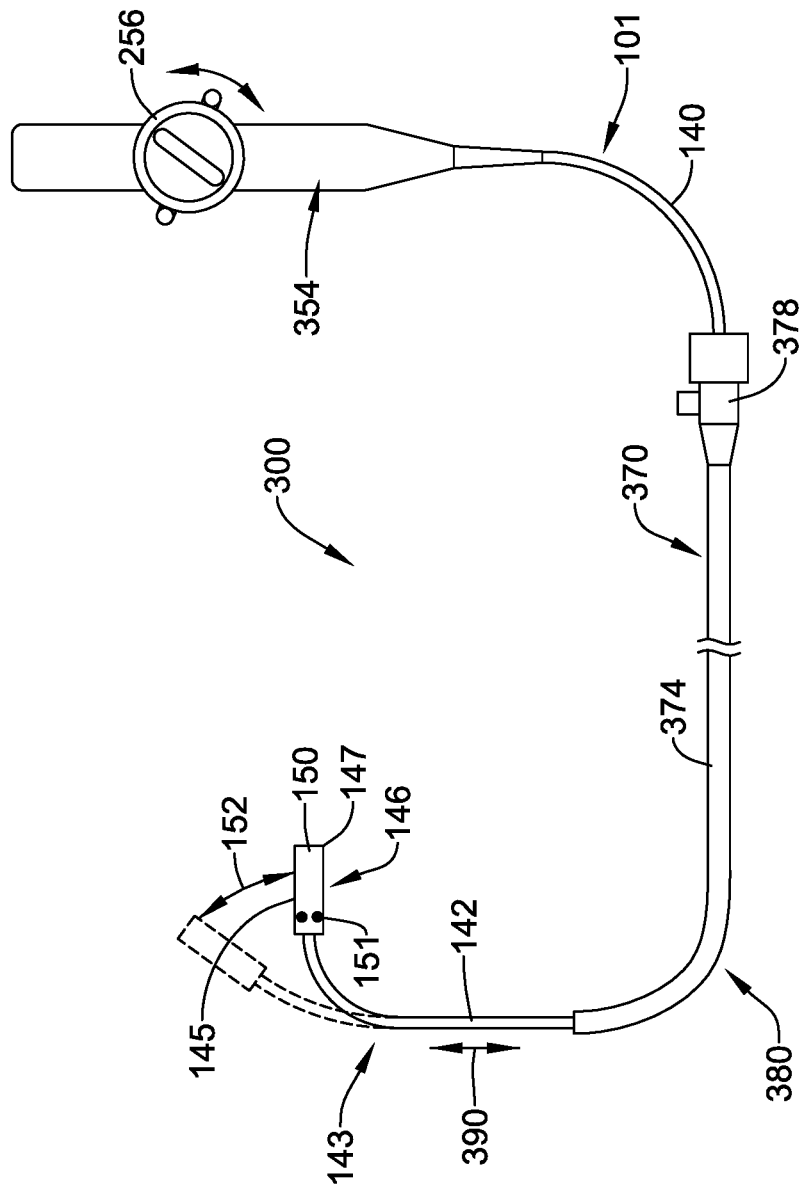
FIG. 4 is a side view of another example delivery device for an implantable leadless cardiac pacing device.

FIG. 4 disclosed another example embodiment of a delivery device 300. The delivery device 300 in this embodiment includes two shaft members that can translate relative to one another, wherein one of the shaft members includes one or more articulation or deflection mechanism(s) (i.e. is deflectable), and the other of the shaft members includes a fixed shape or curve. In this particular embodiment, the delivery device 300 includes an inner tubular member or catheter 101, and an outer tubular member or sheath 370. The inner tubular member 101 may include one or more articulation and/or deflection mechanism(s) such as those discussed above, and the outer tubular member 370 may include one or more predefined or fixed shapes or curve portion(s) 380 along the length thereof. The inner tubular member 101 may be disposed within a lumen of the outer tubular member 370, and the inner and outer tubular members 101 and 370 may translate or be longitudinally movable relative to one another, for example as shown by arrows 390. Deflection of the inner tubular member 101 using the one or more articulation or deflection mechanism(s) influences the shape or orientation of the delivery device 300. Likewise, translation of the inner tubular member 101 relative to the outer tubular member 370 can influence the shape or orientation of the delivery device 300 as well. The combination of the two can provide for desirable compound manipulation of the shape or orientation of the delivery device 300.

In the embodiment shown, the inner tubular member or catheter 101 may be substantially similar in most respects to that of the delivery device 100 shown in FIG. 2, with similar structures numbered the same and with the description related to the embodiment shown in FIG. 2 being equally applicable to this embodiment. In the embodiment shown in FIG. 4, however, the actuation mechanism 256 shown on the hub section 354 of inner tubular member 101 is similar to the actuation mechanism 256 shown in the embodiment in FIG. 3. It should be apparent, however, that other embodiments may include other configurations for the inner tubular member or catheter 101. For example, the inner tubular 101 member could be more similar to that shown in FIG. 3, with two articulation or deflection mechanism(s), or could include more than two articulation or deflection mechanism(s), as discussed above.

The outer tubular member or sheath 370 may include a body portion 374 with a hub 378 attached to the proximal portion thereof, and including one or more predefined or fixed shape or curved portion(s) 380 along the length thereof. In some embodiments, the fixed shape or curved portion(s) 380 are disposed adjacent the distal end of the sheath 370. As such, the fixed shape or curved portion(s) 380 of the sheath 370 may influence the shape and/or orientation of the delivery device 300 as the inner tubular member is translated there through.

It is also contemplated that the deflectable function of the inner and outer tubular members may be reversed. For example, in other embodiments, the inner tubular member 101 may include one or more predefined or fixed shapes or curve portion(s) along the length thereof, and the outer tubular member 370 may include one or more articulation and/or deflection mechanism(s) such as those discussed above. In yet other embodiments, both the inner and outer tubular members 101, 370 may include one or more articulation or deflection mechanism(s) and one or more predefined or fixed shapes or curve portion(s).

In some embodiments, inner tubular member 101 may include a proximal section 140 that may include at least a portion thereof that has an outer diameter that is less than the outer diameter of at least a portion of the holding section 146. The outer tubular member or sheath 370 may have an inner diameter that is the same as, or greater than the outer diameter of the proximal section 140 of the inner tubular member 101, such that the inner tubular member may be disposed there through. However, at least a portion of the holding section 146 may include an outer diameter that is greater than the inner diameter of the outer tubular member or sheath 370, such that the holding section 146 may not fit within the outer tubular member. As a result, in some such embodiments, once the inner tubular member 101 is disposed within the outer tubular member 370, and the hub 354 is attached to the proximal end of the inner tubular member 101, the outer tubular member or sheath 370 may be captured and/or non-removable from being disposed around the inner tubular member.

Figure 5:
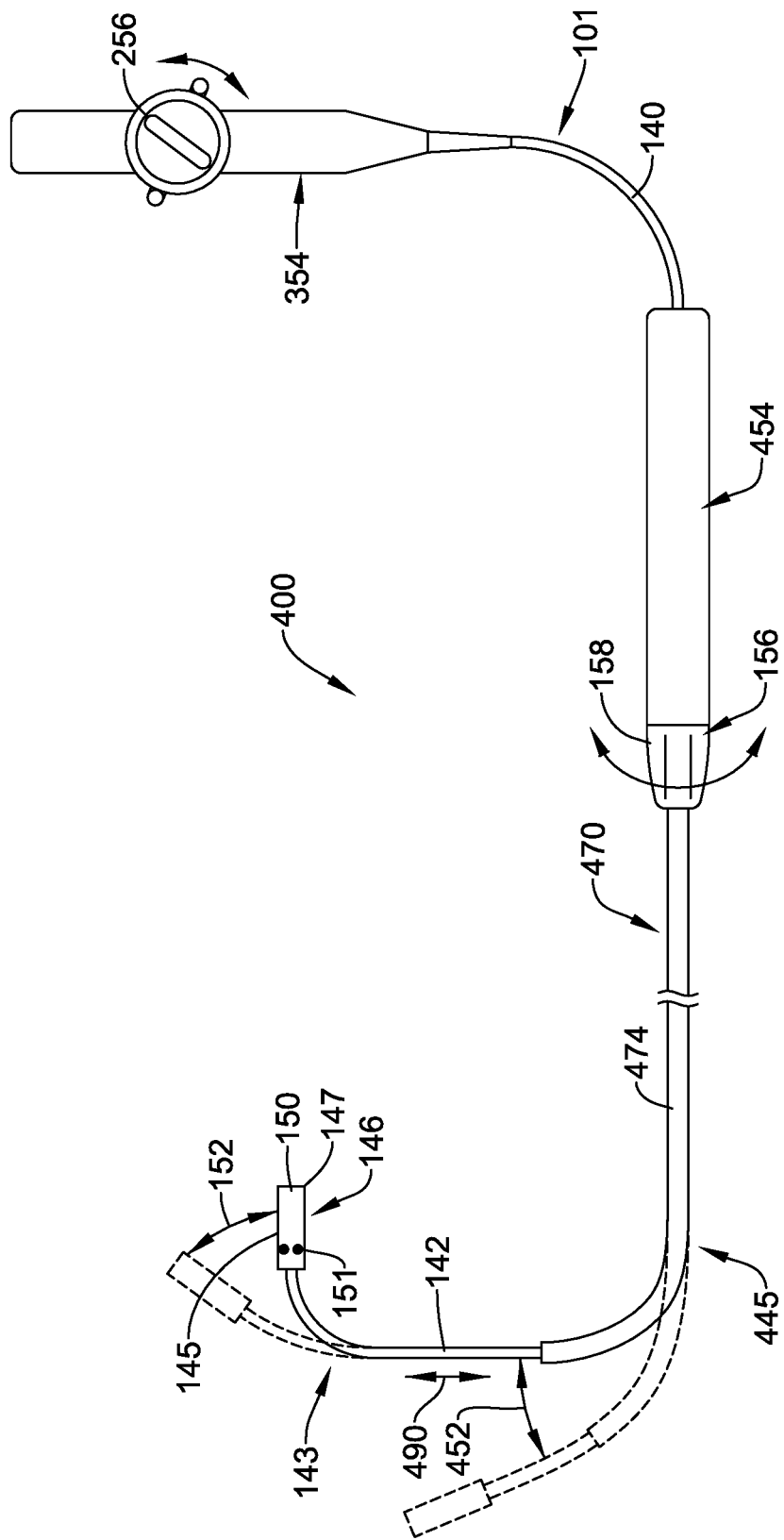
FIG. 5 is a side view of another example delivery device for an implantable leadless cardiac pacing device.

FIG. 5 discloses another example embodiment of a delivery device 400. The delivery device 400 in this embodiment also may include two shaft members that can translate relative to one another, but in this embodiment, both of the shaft members include one or more articulation or deflection mechanism(s) (i.e. are deflectable). In this particular embodiment, the delivery device 400 includes an inner tubular member or catheter 101, and an outer tubular member or sheath 470. The inner tubular member 101 may include one or more articulation and/or deflection mechanism(s) such as those discussed above. In the particular embodiment shown, the inner tubular member 101 may be substantially similar in most respects to that of the inner tubular member 101 shown in FIG. 4, with similar structures numbered the same. However, any other inner member or catheter including a deflection mechanism, including any of those disclosed herein, or others, may be used.

The outer tubular member 470 may also include one or more articulation or deflection mechanism(s) such as any of those discussed above, or others. The outer tubular member or sheath 470 may include a shaft portion 474 with a hub 454 attached to the proximal portion thereof. The deflection mechanism of the outer tubular member 470 may include, for example, a pull wire system such as those as described above, and be configured to impart deflection along a portion of the shaft portion 474, for example along deflection region 445. The hub 454 or other portion of the device 400 may include an actuation mechanism, such as actuation mechanism 156 similar to that discussed above relative to the embodiment shown in FIG. 2, which may be used for example, to control deflection along deflection regions 445.

The inner tubular member 101 may be disposed within a lumen of the outer tubular member 470, and the inner and outer tubular members 101 and 470 may translate or be longitudinally movable relative to one another, for example as shown by arrows 490. Deflection of the inner tubular member 101 using the one or more articulation or deflection mechanism(s) incorporated therein influences the shape or orientation of the delivery device 400. For example, the shaft member 142 of the inner tubular member 101 may be deflected, for example, along deflection region 143 from a first example position indicated in phantom lines, to a second example position indicated in solid lines along a deflection path 152. Deflection of the outer tubular member 470 using the one or more articulation or deflection mechanism(s) incorporated therein influences the shape or orientation of the delivery device 400. For example, the shaft portion 474 of the outer tubular member 470 may be deflected, for example, along deflection region 445 from a first example position indicated in phantom lines, to a second example position indicated in solid lines along a deflection path 452. In addition, translation of the inner tubular member 101 relative to the outer tubular member 470 can also influence the shape or orientation of the delivery device 400. The combination of the deflection mechanisms on both inner and outer members, as well as the translation of the inner and outer member relative to one another can provide for desirable compound manipulation of the shape and/or orientation of the delivery device 400. It is also contemplated that one or both of the inner tubular member 101 and the outer tubular member 470 may include one or more predefined or fixed shapes or curve portion(s) that may further influence the shape and/or orientation of the delivery device 400.

As discussed above regarding FIG. 4, the inner and outer dimensions of the various components may be sized such that once the inner tubular member 101 is disposed within the outer tubular member 470, and the hub 354 is attached to the proximal end of the inner tubular member 101, the outer tubular member or sheath 470 may be captured or non-removable from being disposed around the inner tubular member.

Figure 6:
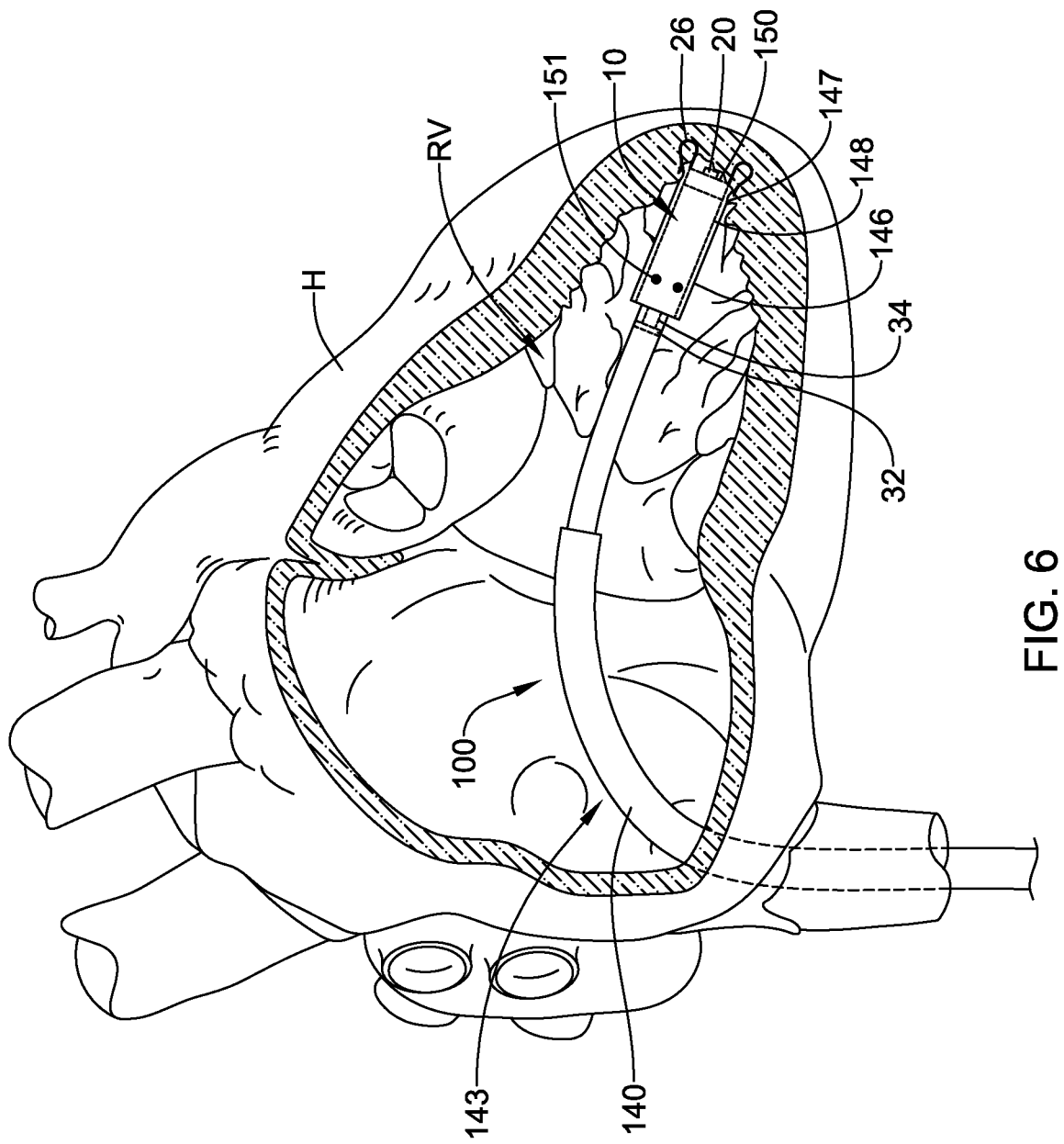
FIG. 6 is a partial cross-sectional side view of the example delivery device of FIGS. 2 and 2A disposed within a heart of a patient for delivering a leadless pacing device therein.

FIG. 6 represents the use of delivery device 100 to deliver an implantable device 10 to the target location in the heart of a patient. Delivery device 100 may be advanced through the vasculature to target region. For example, delivery device 100 may be advanced through a femoral vein, into the inferior vena cava, into the right atrium, through the tricuspid valve, and into the right ventricle. The delivery device 100 may be steered to the target location, and oriented in a delivery configuration using the one or more deflection mechanism and/or one or more predefined or fixed curve portion(s) along the length thereof. Target region may be a portion of the right ventricle, for example, near the apex of the heart. The distal tip 147 may be contacted with or engaged with tissue surrounding the target region. The push member 160 may then be actuated and slid forward such that the head region 164 of push member 160 engages the device 10, and pushes the device 10 toward the opening 150 in the holding section 146. As the device 10 is pushed forward, the anchoring mechanism, such as the one or more hooks 26, may be deployed within the tissue at the target region. The device 10 may be tested at this point, for example, prior to being released or delivered out of the cavity 148. In this context, the conductive pathways 151 that may be present on the delivery device may be useful in allowing for conductive communication between electrodes 20, 22 while the device is still housed within the cavity 148. The device 10 may then be further pushed out of the cavity 148 and released by the delivery device 100. After successful delivery, the delivery device 100 can be withdrawn from the anatomy. It should be understood that the same general procedure may be used for any of the delivery devices and/or systems disclosed herein.

Figure 7:
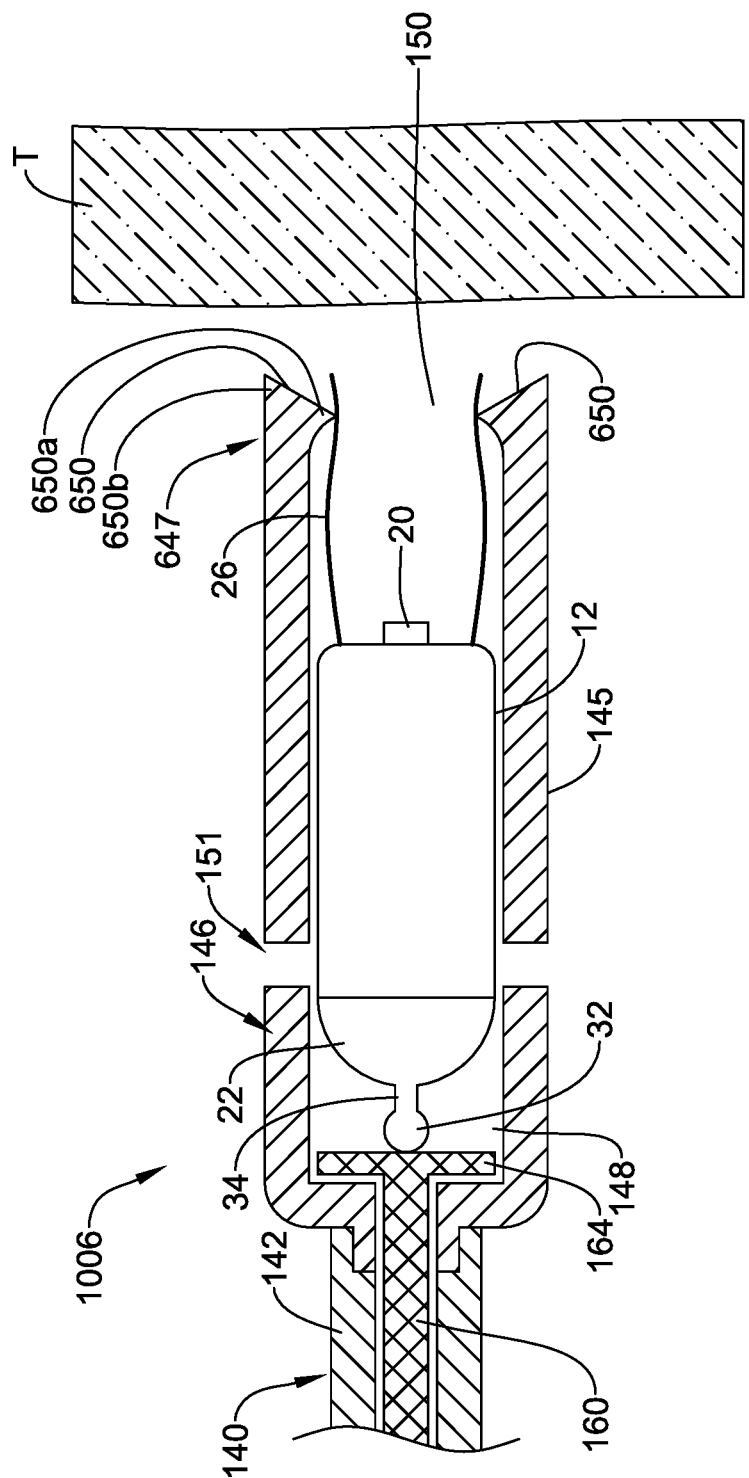
FIG. 7 is a partial cross-sectional side view of the distal portion of another example delivery device, showing the implantable leadless cardiac pacing device disposed therein.
Figure 8:
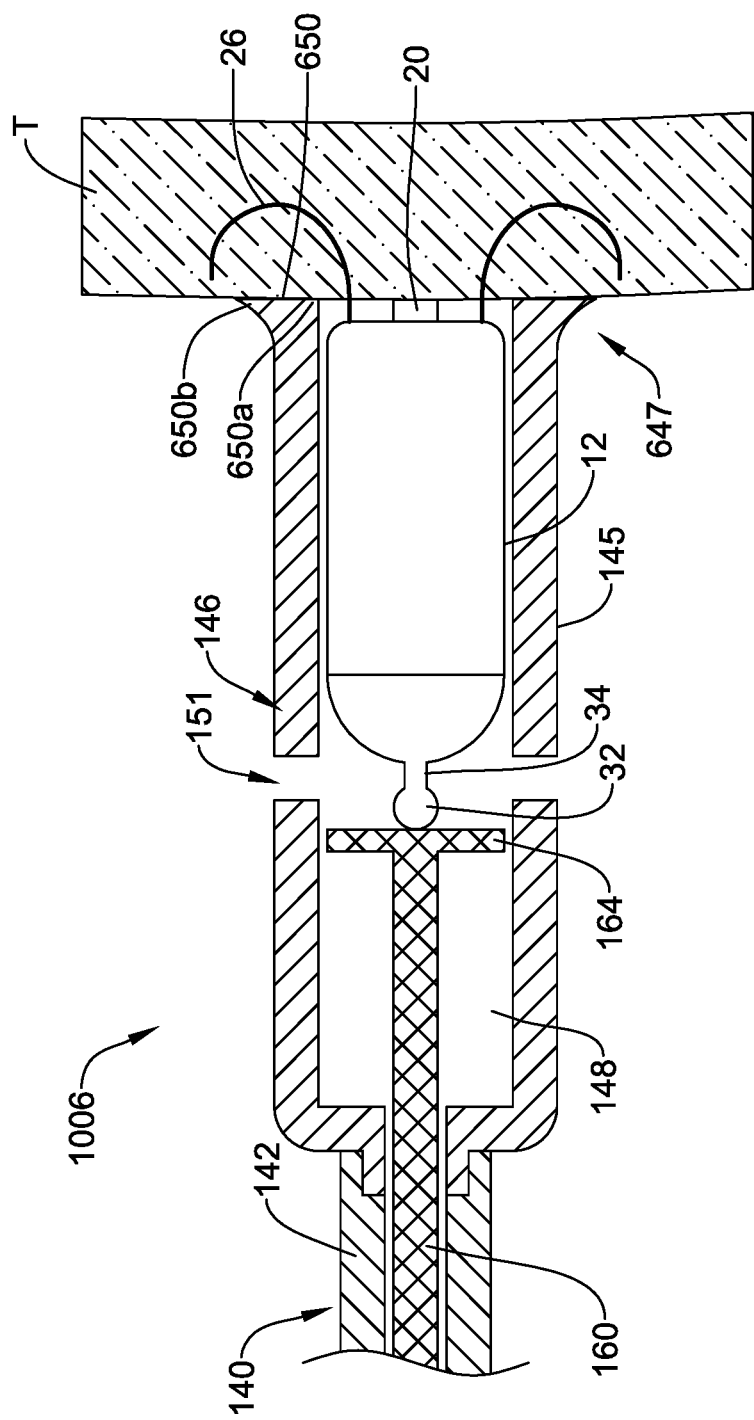
FIG. 8 is a partial cross-sectional side view of the distal portion of the example delivery device of FIG. 7, showing the distal tip engaging the tissue of a patient.

FIG. 7 shows another example embodiment of a delivery device 100b, which is similar in many respects to delivery device 100 described with reference to FIGS. 2 and 2A, with similar structures numbered the same. This embodiment shows a delivery device 100b with a different distal tip structure 647. In this embodiment, the distal tip structure 647 includes a wall thickness that is larger than the wall thickness of the body portion 145 of the distal holding section 146, which may provide for atraumatic attributes. Additionally, the distal tip 647 includes an angled distal end surface 650, for example, that defines an acute angle relative to a longitudinal axis of the distal holding section 146. In the embodiment shown, the angled distal end surface 650 is angled inwardly, such that the radially outward distalmost extent of the tip 650a is disposed distally of the radially inward distalmost extent of the tip 650b. (e.g. edge or corner 650a is more distal than edge or corner 650b). In other embodiments, the angled distal end surface 650 may be angled outwardly, such that the configuration of 650a and 650b is reversed from that described above. The angled distal end surface 650 may be configured to flatten against a surface of tissue T of a patient when brought into contact with the tissue surface and a sufficient force is applied. The distal tip portion 647 may be deformable to provide an atraumatic surface for engagement with a tissue of a patient. For example, refer now to FIG. 8, which shows the distal tip structure 647 of the delivery device 100b being brought into contact with the surface of the tissue T. As can be appreciated, the angled distal end surface 650 has flattened against a surface of tissue T.

The materials that can be used for the various components of the delivery devices, such as delivery devices 100/100b/200/300/400 (and/or other delivery structures disclosed herein) and the various members disclosed herein may include those commonly associated with medical devices. For simplicity purposes, the following discussion makes reference the delivery devices 100/100b/200/300/400 and components of thereof. However, this is not intended to limit the devices and methods described herein, as the discussion may be applied to other similar delivery systems and/or components of delivery systems or devices disclosed herein.

The delivery devices 100/100b/200/300/400 and/or other components of delivery system may be made from a metal, metal alloy, polymer (some examples of which are disclosed below), a metal-polymer composite, ceramics, combinations thereof, and the like, or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the polymer can be blended with a liquid crystal polymer (LCP). For example, the mixture can contain up to about 6 percent LCP.

Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

As alluded to herein, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear that the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also can be distinguished based on its composition), which may accept only about 0.2 to 0.44 percent strain before plastically deforming.

In some embodiments, the linear elastic and/or non-super-elastic nickel-titanium alloy is an alloy that does not show any martensite/austenite phase changes that are detectable by differential scanning calorimetry (DSC) and dynamic metal thermal analysis (DMTA) analysis over a large temperature range. For example, in some embodiments, there may be no martensite/austenite phase changes detectable by DSC and DMTA analysis in the range of about −60 degrees Celsius (° C.) to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Some examples of nickel titanium alloys are disclosed in U.S. Pat. Nos. 5,238,004 and 6,508,803, which are incorporated herein by reference. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In at least some embodiments, portions or all of the delivery devices 100/100b/200/300/400 and/or other components of delivery system may be doped with, made of, or otherwise include a radiopaque material. Radiopaque materials are understood to be materials capable of producing a relatively bright image on a fluoroscopy screen or another imaging technique during a medical procedure. This relatively bright image aids the user of the delivery devices 100/100b/200/300/400 in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the delivery devices 100/100b/200/300/400 to achieve the same result.

In some embodiments, a degree of Magnetic Resonance Imaging (Mill) compatibility is imparted into the delivery devices 100/100b/200/300/400. For example, delivery devices 100/100b/200/300/400, or portions or components thereof, may be made of a material that does not substantially distort the image and create substantial artifacts (i.e., gaps in the image). Certain ferromagnetic materials, for example, may not be suitable because they may create artifacts in an Mill image. The delivery devices 100/100b/200/300/400, or portions thereof, may also include and/or be made from a material that the Mill machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The invention's scope is, of course, defined in the language in which the appended claims are expressed.

What is claimed is:

1. A delivery device for delivering an implantable leadless pacing device, the delivery device comprising:
a proximal hub portion;
a proximal section coupled to and extending distally from the proximal hub portion, the proximal section including an outer tubular member and an inner tubular member slidably disposed in a lumen of the outer tubular member and axially translatable relative to the outer tubular member, the outer tubular member including a deflection mechanism configured to deflect at least a portion of the outer tubular member;
a distal holding section extending distally of a distal end of the proximal section, the distal holding section including a proximal end fixed to a distal end of the inner tubular member and axially translatable therewith, the distal holding section having an outer surface with and outer diameter greater than an outer diameter of the inner tubular member, the distal holding section having an inner surface defining a cavity therein for receiving an implantable leadless pacing device;
a push member slidably disposed within a lumen of the inner tubular member;
wherein the push member is configured to engage the implantable leadless pacing device and deploy the implantable leadless pacing device out of the cavity of the distal holding section;
wherein the distal holding section includes a wall extending from the outer surface to the inner surface, the wall comprising one or more conductive pathways defined in the wall that are spaced proximally from a distal end of the distal holding section;
wherein the one or more conductive pathways are formed of a conductive material.

2. The delivery device of claim 1, wherein the distal holding section includes a body portion and a distal tip portion distal of the body portion;
wherein the body portion comprises a first polymer material and the distal tip portion comprises a second polymer material different from the first polymer material.

3. The delivery device of claim 2, wherein the second polymer material has a durometer less than that of the first polymer material.

4. The delivery device of claim 2, wherein the first polymer material extends to the outer surface of the distal holding section throughout the body portion.

5. The delivery device of claim 4, wherein the first polymer material extends to the inner surface of the distal holding section throughout the body portion.

6. The delivery device of claim 2, wherein the distal tip portion includes a wall thickness that is greater than a wall thickness of at least a portion of the body portion.

7. The delivery device of claim 2, wherein the distal tip portion includes an angled distal end surface that defines an acute angle relative to a longitudinal axis of the distal holding section.

8. The delivery device of claim 7, wherein the angled distal end surface is configured to flatten against a tissue surface of a patient when brought into contact with the tissue surface.

9. The delivery device of claim 2, wherein the distal tip portion is deformable to provide an atraumatic surface for engagement with a tissue of a patient.

10. The delivery device of claim 1, wherein the conductive material is a conductive metal.

11. A delivery device for delivering an implantable leadless pacing device, the delivery device comprising:
a catheter shaft;
a push member slidably disposed within a lumen of the catheter shaft; and
a distal holding section positioned at a distal end of the catheter shaft and axially translatable therewith, the distal holding section including a wall defining a cavity for receiving the implantable leadless pacing device, wherein the wall comprises a polymeric material and one or more conductive pathways defined in the wall that are spaced proximally from a distal end of the distal holding section, wherein the one or more conductive pathways comprise a conductive material;
wherein the push member is configured to engage the implantable leadless pacing device and deploy the implantable leadless pacing device out of the cavity of the distal holding section.

12. The delivery device of claim 11, wherein the distal holding section has an outer diameter greater than an outer diameter of the catheter shaft.

13. The delivery device of claim 11, wherein the conductive material is a conductive metal.

14. The delivery device of claim 11, wherein the distal holding section includes a body portion and a distal tip portion distal of the body portion;
wherein the body portion comprises a first polymer material and the distal tip portion comprises a second polymer material different from the first polymer material.

15. The delivery device of claim 14, wherein the second polymer material has a durometer less than that of the first polymer material.

16. The delivery device of claim 14, wherein the first polymer material extends to the outer surface of the distal holding section throughout the body portion.

17. The delivery device of claim 16, wherein the first polymer material extends to the inner surface of the distal holding section throughout the body portion.

18. The delivery device of claim 17, wherein the distal tip portion is devoid of the first polymer material.

19. The delivery device of claim 18, wherein the distal tip portion includes a wall thickness that is greater than a wall thickness of at least a portion of the body portion.

20. A delivery device for delivering an implantable leadless pacing device, the delivery device comprising:
a catheter shaft; and
a distal holding section positioned at a distal end of the catheter shaft and axially translatable therewith, the distal holding section including a wall defining a cavity for receiving the implantable leadless pacing device, wherein the wall comprises a polymeric material and one or more conductive pathways defined in the wall that are spaced proximally from a distal end of the distal holding section, wherein the one or more conductive pathways comprise a conductive metal;
wherein the one or more conductive pathways allow for conductive communication between first and second electrodes of the implantable leadless pacing device through the distal opening and the one or more conductive pathways, respectively.

* * * * *